United States Patent
Ray

(10) Patent No.: US 12,102,712 B2
(45) Date of Patent: Oct. 1, 2024

(54) COMPOSITION AND METHOD FOR TREATING FUNGAL SKIN CONDITIONS AND INFLAMMATION

(71) Applicant: CMPD LICENSING LLC, Conroe, TX (US)

(72) Inventor: Jay Richard Ray, Conroe, TX (US)

(73) Assignee: CMPD Licensing LLC, Conroe, TX (US)

( * ) Notice: Subject to any disclaimer, the term of this patent is extended or adjusted under 35 U.S.C. 154(b) by 698 days.

(21) Appl. No.: 17/306,273

(22) Filed: May 3, 2021

(65) Prior Publication Data
US 2022/0110859 A1   Apr. 14, 2022

Related U.S. Application Data

(63) Continuation of application No. 15/273,276, filed on Sep. 22, 2016, now abandoned.

(51) Int. Cl.
| | |
|---|---|
| A61K 31/56 | (2006.01) |
| A61K 9/00 | (2006.01) |
| A61K 9/06 | (2006.01) |
| A61K 31/4174 | (2006.01) |
| A61K 31/496 | (2006.01) |
| A61K 31/573 | (2006.01) |
| A61K 31/58 | (2006.01) |
| A61K 47/10 | (2017.01) |

(52) U.S. Cl.
CPC .............. *A61K 9/0014* (2013.01); *A61K 9/06* (2013.01); *A61K 31/4174* (2013.01); *A61K 31/496* (2013.01); *A61K 31/56* (2013.01); *A61K 31/573* (2013.01); *A61K 31/58* (2013.01); *A61K 47/10* (2013.01)

(58) Field of Classification Search
CPC .... A61K 9/0014; A61K 9/06; A61K 31/4174; A61K 31/496; A61K 31/56; A61K 31/573; A61K 31/58
See application file for complete search history.

(56) References Cited

FOREIGN PATENT DOCUMENTS

WO    WO-2010069519 A1 *  6/2010  ........... A61K 9/0014

OTHER PUBLICATIONS

Schaller et al. Topical antifungal-corticosteroid combination therapy for the treatment of superficial mycoses: Conclusions of an expert panel meeting. Mycoses 2016;59:365-73 (Year: 2016).*
Ference et al. Am Fam Physician. 2009;79(2):135-140 (Year: 2009).*

* cited by examiner

*Primary Examiner* — Matthew P Coughlin
*Assistant Examiner* — Ashli Ariana Chicks
(74) *Attorney, Agent, or Firm* — Akerman LLP

(57) ABSTRACT

A topical composition for treating fungal skin infections with associated inflammation may include making or administering to the affected skin area an antifungal and steroid, such as a corticosteroid. Certain compositions may include antifungals such as itraconazole or econazole and corticosteroids such as fluticasone, fluocinonide, or clobetasol. The antifungal and steroid may be within a cream. In one example, a commercially available econazole nitrate cream may be used in conjunction with a commercially available fluocinonide cream or commercially available clobetasol cream to treat the affected skin area.

7 Claims, No Drawings

COMPOSITION AND METHOD FOR TREATING FUNGAL SKIN CONDITIONS AND INFLAMMATION

CROSS-REFERENCE TO RELATED APPLICATIONS

This patent application is a continuation of U.S. patent application Ser. No. 15/273,276, filed Sep. 22, 2016, the contents of which are hereby incorporated herein by reference.

TECHNICAL FIELD

The present application is directed to compositions and methods for topical treatment of fungal skin conditions and inflammation. More specifically, the present application is directed to compositions and methods for treating fungal skin conditions and inflammation with a topical composition including an antifungal and corticosteroid.

BACKGROUND

Fungal infections of the skin are common. Topically applied antifungals may be used to combat such infections, which employ three general mechanisms of action: cell membrane disruption, inhibition of cell division and inhibition of cell wall formation.

Corticosteroids play a role in cellular signaling, immune function, inflammation, and protein regulation. Corticosteroids may be used combat inflammation of the skin. Hydrocortisone, for example, may be topically applied to skin to reduce swelling, itching, and redness due to poison ivy, allergies, rashes, eczema, and insect bites. While the mechanism of the anti-inflammatory activity of topical steroids, in general, is unclear, corticosteroids are thought to act by the induction of phospholipase A inhibitory proteins, collectively called lipocortins. It is postulated that these proteins control the biosynthesis of potent mediators of inflammation such as prostaglandins and leukotrienes by inhibiting the release of their common precursor, arachidonic acid, which is released from membrane phospholipids by phospholipase $A_2$. Topical corticosteroids can be absorbed from normal intact skin. The extent of percutaneous absorption of topical corticosteroids is determined by many factors including the vehicle and the integrity of the epidermal barrier. For example, inflammation and/or other disease processes in the skin may increase percutaneous absorption.

SUMMARY

In one aspect, a method of compounding a topical composition for treating a fungal skin condition having associated inflammation includes combining fluticasone, or pharmaceutically acceptable salt, ester, or derivative thereof, itraconazole, or pharmaceutically acceptable salt, ester, or derivative thereof, and a topical base. The itraconazole may be combined in an amount between approximately 3% and approximately 8% by weight of the compounded topical composition. The fluticasone may be combined in an amount between approximately 0.5% and 2.5% by weight of the compounded topical composition.

In one example, the topical base comprises Base C and a water miscible base. The topical base may comprise water miscible base and Base C in a ratio between approximately 8:1 and approximately 9:1. In one formulation, the water miscible base comprises Spira-Wash™ Gel. The topical base may be combined with the fluticasone and itraconazole in an amount between approximately 5% and approximately 15% Base C by weight of the compounded topical composition and between approximately 90% and approximately 75% Spira-Wash™ Gel by weight of the compounded topical composition. In one particular example, itraconazole may be combined in an amount approximately 5% by weight of the compounded topical composition, fluticasone may be combined in an amount approximately 1% by weight of the compounded topical composition, Base C may be combined in an amount approximately 10% by weight of the compounded topical composition, and Spira-Wash™ Gel may be combined in an amount approximately 84% by weight of the compounded topical composition. In one formulation, the itraconazole and fluticasone are combined with the topical base or components thereof in the form of bulk powders.

In another aspect, a topical composition for treating a fungal skin condition having associated inflammation includes between approximately 3% and approximately 8% by weight itraconazole, or pharmaceutically acceptable salt, ester, or derivative thereof, between approximately 0.5% and 2.5% by weight fluticasone, or pharmaceutically acceptable salt, ester, or derivative thereof, and a topical base. In one example, the topical base comprises Base C and a water miscible base. For example, in one embodiment, the topical base comprises water miscible base and Base C in a ratio between approximately 8:1 and approximately 9:1. In one formulation, the water miscible base comprises Spira-Wash™ Gel. In one embodiment, the topical composition comprises between approximately 5% and approximately 15% by weight Base C and between approximately 90% and approximately 75% by weight Spira-Wash™ Gel. In one example, the topical composition comprises approximately 5% by weight itraconazole, approximately 1% by weight fluticasone, approximately 10% by weight Base C, and approximately 84% by weight Spira-Wash™ Gel.

In yet another aspect, a method of treating a patient for a fungal skin condition with associated inflammation includes applying Econazole Nitrate Cream 1% to the affected skin area, and applying at least one of a Fluocinonide Cream 0.1% or Clobetasol Propionate Cream, Gel, or Ointment 0.05% to the affected skin area. In various embodiments, applying the Econazole Nitrate Cream 1% comprises applying up to 3 gm of the cream to the affected skin area two times daily. Applying the Fluocinonide Cream 0.1% may include applying up to 1 gm of the cream to the affected skin area two times daily. Applying the Clobetasol Propionate Cream, Gel, or Ointment 0.05% may include applying up to 1 gm of the cream, gel, or ointment to the affected skin area two times daily. In one formulation, the Clobetasol Propionate Cream, Gel, or Ointment 0.05% is Clobetasol Propionate Ointment 0.05%. In one example, applying the Econazole Nitrate Cream 1% comprises applying up to 3 gm of the cream to the affected skin area two times daily. Applying the at least one of Fluocinonide Cream 0.1% or Clobetasol Propionate Cream, Gel, or Ointment 0.05% may comprise applying up to 1 gm of Fluocinonide Cream 0.1% or 1 gm of Clobetasol Propionate Ointment 0.05% to the affected skin area two times daily. In a further example, applying Econazole Nitrate Cream 1% and the at least one of the Fluocinonide Cream 0.1% or Clobetasol Propionate Ointment 0.05% comprising applying the Econazole Nitrate Cream 1% and the at least one of the Fluocinonide Cream 0.1% or Clobetasol Propionate Ointment 0.05% at substantially the same time to the affected skin area.

DESCRIPTION

The present disclosure describes pharmaceutical compositions comprising topical compositions for treating fungal skin infections accompanied by inflammation. The topical compositions may include one or more creams comprising an antifungal and a corticosteroid. In some embodiments, the topical compositions may include a compounded topical cream comprising the antifungal and corticosteroid. In further embodiments, the topical compositions may comprise additional actives such as one or more, including multiples, of an antibiotic, antihistamine, nerve depressant, local anesthetic, NSAID, anticonvulsant, antidepressant, muscle relaxant, or other active ingredient.

In various embodiments, the topical composition comprises a base. The base may be a base suitable for topical application to a body surface such as a foam, cream, gel, lotion, ointment, or emulsion (oil-in-water or water-in-oil), for example, suitable for topical application to skin or nails. For brevity, such bases may be referred to herein as a topical base. Thus, unless otherwise specified, a topical base may include bases comprising foams, gels, lotions, ointments, creams, or emulsions (oil-in-water or water-in-oil). Similarly, various topical compositions comprising an active agent in a vehicle are described herein as an "active agent" cream. However, unless specified otherwise, e.g., reference to a specific Active Agent Cream, Gel, or Lotion, such active agent creams may include the named active agent in a foam, gel, lotion, ointment, cream, or emulsion (oil-in-water or water-in-oil) vehicle.

In some embodiments, the topical base comprises polyethylene glycol (PEG). For example, the topical base may comprise Base C (polyethylene glycol 300 MW, NF liquid). Polyethylene glycol 300, NF, which may sometimes also be referred to as PEG-6 or PEG, is highly water soluble and may act as a solvent, plasticizer, or surfactant in creams such as ointments. In other embodiments, the topical base is PEG-free. In these or other embodiments, the topical base may comprise a silicon or silicon variant while in other embodiments the topical base may be silicon-free. An example topical base comprising a foam may include a propellant such as butane. Topical bases comprising a foam may also comprise additional characteristics such as that of an emulsion, such as an oil-in-water emulsion. In one example, the topical base comprises a cream, lotion, gel, or ointment, which may include a water soluble/miscible, absorption, water-in-oil emulsion, or oil-in-water emulsion. Example topical bases may include foams, gels, lotions, ointments, creams including or comprising carbomer, propylene glycol, hydrophilic petrolatum, white tetrolatum, white petrolatum, hydrophilic, hydrogel, white ointment, anhydrous lanolin, hydrous lanolin, PEG, sorbitan sesquioleate, or combinations thereof.

In various embodiments, the topical base comprises one or more commercially available topical bases, e.g., commercially manufactured topical bases available to compounders of pharmaceuticals. For example, in one embodiment, the compounded topical composition comprises the topical base Spira-Wash™ Gel or Lipoderm®, both of which are marketed by Professional Compounding Centers of America (PCCA), Houston, TX Spira-Wash™ Gel is a water miscible topical base including a blend of Meadowsweet Flower Extract, which is rich in phenolic compounds, salicylates, and flavonoids, in a polyethylene glycol (PEG) ointment base. Spira-Wash™ Gel is a soft, adherent gel, which is easily water washable. It has potential use in dermatologic formulations for different applications, such as wound care, an occlusive agent, a topical humectant or infection treatment. Lipoderm® may include Lipoderm® or Lipoderm® derivatives such as ActiveMax™, Anhydrous, or High Molecular Weight Lipoderm®. Lipoderm® ActiveMax™, for example, and may include water, cetearyl alcohol, plukenetia volubilis seed oil, isopropyl myristate, propylheptyl caprylate, sodium stearoyl glutamate, PEG-8/SMDI copolymer, PEG-100 stearate, glyceryl stearate, glycerin, tocopheryl acetate, lecithin hydrogenated lecithin, *Populus tremuloides* bark extract, *Lonicera japonica* (honeysuckle) flower extract, *Lonicera caprifolium* (honeysuckle) flower extract, leuconostoc/radish root ferment filtrate, *Pentaclethra macroloba* seed oil, *Butyrospermum parkii* (shea) butter, *Carthamus tinctorius* (safflower) seed oil, *Cocos nucifera* (coconut) oil, tocopherol, ascorbyl palmitate, squalane, ceramide 3, alcohol, glyceryl stearate, caprylic/capric triglyceride, xanthan gum, gluconolactone, sodium dehydroacetate, disodium EDTA, BHT.

As introduced above, the topical composition includes a corticosteroid. In various embodiments, the corticosteroid is selected from fluticasone, clobetasol, triamcinolone, betamethasone, dexamethasone, flunisolide, prednisone, prednisolone, methylprednisolone, fluocinolone, diflorasone, halcinonide, desoximetasone, diflucortolone, flucloronide, fluocinonide, fluocortolone, fluprednidene, flurandrenolide (flurandrenolone), clobetasol, clobetasone, alclometasone, flumethasone, fluocortolone, amcinonide, beclomethasone, difluprednate, prednicarbate, flurandrenolide, mometasone, desonide, or combinations thereof. In one embodiment, the composition includes a corticosteroid selected from fluticasone, clobetasol, fluocinonide, or combinations thereof.

The corticosteroid may be present in the topical composition in an amount between approximately 0.001% to approximately 2.5%, such as approximately 0.001% to approximately 0.00125%, approximately 0.001% to approximately 0.005%, approximately 0.00125% to approximately 0.005%, approximately 0.00125% to approximately 0.025%, approximately 0.025% to approximately 2.5%, approximately 0.025% to approximately 2%, approximately 0.025% to approximately 1.5%, approximately 0.025% to approximately 1%, approximately 0.025% to approximately 0.5%, approximately 0.025% to approximately 0.05%, approximately 0.05% to approximately 2.5%, approximately 0.05% to approximately 2%, approximately 0.05% to approximately 1.5%, approximately 0.05% to approximately 1%, approximately 0.05% to approximately 0.5%, approximately 0.5% to approximately 2.5%, approximately 0.5% to approximately 2%, approximately 0.5% to approximately 1.5%, approximately 0.5% to approximately 1%, approximately 1% to approximately 2.5%, approximately 1% to approximately 2%, approximately 1% to approximately 1.5%, approximately 1.5% to approximately 2.5%, approximately 1.5% to approximately 2%, approximately 1.5% to approximately 2.5% by weight, or approximately 0.001%, approximately 0.00125%, approximately 0.005%, approximately 0.01%, approximately 0.05%, approximately 0.1%, approximately 0.5%, approximately 1%, approximately 1.5%, approximately 2%, or approximately 2.5%.

The topical composition may also include an antifungal in addition to the corticosteroid. In various embodiments, the antifungal is or comprises an azole. The azole may be added alone or in combination with additional antifungals. For example, the antifungal may comprise an azole selected from itraconazole, clotrimazole, econazole, oxiconazole, ketoconazole, miconazole, voriconazole, sulconazole, fluconazole. In the above or other formulations, the antifungal may comprise one or more antifungal actives selected from ciclopirox, amphotericin B, Nystatin, terbinafine, amorolfine, flucytosine, or combination thereof. According to various embodiments, the topical composition comprises a weight percent of antifungal agent between approximately 0.5% to approximately 8%, approximately 0.5% to approximately 7.5%, approximately 0.5% to approximately 7%, approximately 0.5% to approximately 6.5%, approximately 0.5% to approximately 6%, approximately 0.5% to approximately 5.5%, approximately 0.5% to approximately 5%, approximately 0.5% to approximately 4.5%, approximately 0.5% to approximately 4%, approximately 0.5% to approximately 3.5%, approximately 0.5% to approximately 3%, approximately 0.5% to approximately 2.5%, approximately 0.5% to approximately 1.5%, approximately 0.5% to approximately 1%, approximately 0.5% to approximately 0.75%, approximately 0.75% to approximately 8%, approximately 0.75% to approximately 7.5%, approximately 0.75% to approximately 7%, approximately 0.75% to approximately 6.5%, approximately 0.75% to approximately 6%, approximately 0.75% to approximately 5.5%, approximately 0.75% to approximately 5%, approximately 0.75% to approximately 4.5%, approximately 0.75% to approximately 4%, approximately 0.75% to approximately 3.5%, approximately 0.75% to approximately 3%, approximately 0.75% to approximately 2.5%, approximately 0.75% to approximately 1.5%, approximately 0.75% to approximately 1%, approximately 1% to approximately 8%, approximately 1% to approximately 7.5%, approximately 1% to approximately 7%, approximately 1% to approximately 6.5%, approximately 1% to approximately 6%, approximately 1% to approximately 5.5%, approximately 1% to approximately 5%, approximately 1% to approximately 4.5%, approximately 1% to approximately 4%, approximately 1% to approximately 3.5%, approximately 1% to approximately 3%, approximately 1% to approximately 2.5%, approximately 1% to approximately 1.5%, approximately, 2% to approximately 8%, approximately 2% to approximately 7.5%, approximately 2% to approximately 7%, approximately 2% to approximately 6.5%, approximately 2% to approximately 6%, approximately 2% to approximately 5.5%, approximately 2% to approximately 5%, approximately 2% to approximately 4.5%, approximately 2% to approximately 4%, approximately 2% to approximately 3.5%, approximately 2% to approximately 3%, approximately 2% to approximately 2.5%, approximately, 3% to approximately 8%, approximately 3% to approximately 7.5%, approximately 3% to approximately 7%, approximately 3% to approximately 6.5%, approximately 3% to approximately 6%, approximately 3% to approximately 5.5%, approximately 3% to approximately 5%, approximately 3% to approximately 4.5%, approximately 3% to approximately 4%, approximately 3% to approximately 3.5%, approximately 5% to approximately 8%, approximately 5% to approximately 7.5%, approximately 5% to approximately 6.5%, approximately 5% to approximately 6%, approximately 5% to approximately 5.5%, approximately 6% to approximately 8%, approximately 6% to approximately 7.5%, approximately 6% to approximately 7%, approximately 6% to approximately 6.5%, approximately 7% to approximately 8%, approximately 7% to approximately 7.5% by weight, or approximately 0.5%, approximately 0.75%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, or approximately 8%.

Various embodiments of the topical composition, may include any combination of the above corticosteroids and antifungals in a topical base, such as any one or combination of the topical base creams described above. For example, the topical composition may include a corticosteroid and antifungal identified above in a topical base cream comprising Spira-Wash™ Gel. In a further example, the topical composition includes the steroid and antifungal in a topical base comprising Spira-Wash™ Gel and Base C. The ratio of Spira-Wash™ Gel to Base C may be between 10:1 to 5:1, for example. In one embodiment, the ratio of Spira-Wash™ Gel to Base C is between 9:1 and 8:1. The topical base cream may make up the remainder by weight of the topical composition noting include the steroid, antifungal, and any additional medications or inactives. In some embodiments, the topical composition comprises greater than 60%, 65%, 70%, 75%, 80%, 84%, 88%, 90%, 92%, 94%, 95% by weight topical base.

In various embodiments, the corticosteroid comprises fluticasone, or pharmaceutically acceptable salt, ester, or derivative thereof. For example, fluticasone may be present in the topical composition in an amount between approximately 0.5% to approximately 2.5%, approximately 0.5% to approximately 2%, approximately 0.5% to approximately 1.5%, approximately 0.5% to approximately 1%, approximately 1% to approximately 2.5%, approximately 1% to approximately 2%, approximately 1% to approximately 1.5%, approximately 1.5% to approximately 2.5%, approximately 1.5% to approximately 2%, approximately 1.5% to approximately 2.5%, such as approximately 0.5%, approximately 1%, approximately 1.5%, approximately 2%, or approximately 2.5% by weight of the topical composition. In these or further embodiments, the antifungal comprises the azole itraconazole, or pharmaceutically acceptable salt, ester, or derivative thereof. For example, itraconazole may be present in the topical composition in an amount between approximately 3% to approximately 8%, approximately 3% to approximately 7.5%, approximately 3% to approximately 7%, approximately 3% to approximately 6.5%, approximately 3% to approximately 6%, approximately 3% to approximately 5.5%, approximately 3% to approximately 5%, approximately 3% to approximately 4.5%, approximately 3% to approximately 4%, approximately 3% to approximately 3.5%, approximately 5% to approximately 8%, approximately 5% to approximately 7.5%, approximately 5% to approximately 6.5%, approximately 5% to approximately 6%, approximately 5% to approximately 5.5%, approximately 6% to approximately 8%, approximately 6% to approximately 7.5%, approximately 6% to approximately 7%, approximately 6% to approximately 6.5%, approximately 7% to approximately 8%, approximately 7% to approximately 7.5%, or approximately 3%, approximately 3.5%, approximately 4%, approximately 4.5%, approximately 5%, approximately 5.5%, approximately 6%, approximately 6.5%, approximately 7%, approximately 7.5%, or approximately 8% by weight of the topical composition. The topical composition may further comprise the fluticasone and itraconazole in a topical base cream, such as any one or combination of the topical base creams described above. For example, the topical composition may include the steroid and antifungal in a topical base comprising Spira-Wash™ Gel. In a further example, the topical composition includes the steroid and antifungal in a topical base comprising Spira-Wash™ Gel and Base C. The ratio of Spira-Wash™ Gel to Base C may be between 10:1 to 5:1, for example. In one embodiment, the ratio of Spira-Wash™ Gel to Base C is between 9:1 and 8:1. The topical base may make up the remainder by weight of the topical composition that does not include the steroid, antifungal, and any additional medications or inactives. In some embodiments, the topical composition comprises greater than 60%, 65%, 70%, 75%, 80%, 84%, 88%, 90%, 92%, 94%, 95% by weight topical base cream. In one embodiment, the topical composition comprises approximately 5% itraconazole by weight, approximately 1 fluticasone by weight, approximately 10% Base C by weight, and approximately 84% Spira-Wash™ Gel by weight.

In various embodiments, the topical composition may include a commercially available antifungal cream comprising a econazole nitrate cream. Econazole nitrate cream is indicated for topical application and includes very little systemic absorption. Econazole nitrate cream is a commercially available antifungal cream indicated in the treatment of tinea pedis, tinea cruris, and tinea corporis caused by *Trichophyton rubrum, Trichophyton mentagrophytes, Trichophyton tonsurans, Microsporum canis, Microsporum audouini, Microsporum gypseum*, and *Epidermophyton floccosum*, in the treatment of cutaneous candidiasis, and in the treatment of tinea versicolor. One example of commercially manufactured econazole nitrate cream is Econazole Nitrate Cream 1%. Among other sources, Econazole Nitrate Cream 1% is manufactured by Taro Pharmaceuticals Inc., Brampton, Ontario, Canada L6T 1C1 and distributed by Taro Pharmaceuticals U.S.A., Inc., Hawthorne, NY 10532. Other manufactures or distributers may be used. Econazole Nitrate Cream 1% includes econazole nitrate 1% (10 mg per 1 g) in a water-miscible base consisting of apricot kernel oil/PEG-6, benzoic acid, butylated hydroxytoluene, mineral oil, PEG-6-32 stearate/glycol stearate and purified water.

In one embodiment, the topical composition includes Econazole Nitrate Cream 1% and one or more steroids selected from those identified above or elsewhere herein and in an amount provided above or elsewhere herein. For example, the topical composition may include Econazole Nitrate Cream 1% and a corticosteroid selected from fluticasone, clobetasol, fluocinonide, or combinations thereof in an amount between approximately 0.001% to approximately 2.5% by weight of the topical composition.

In various embodiments, the topical composition may include a commercially available corticosteroid cream. For example, the topical composition may include a fluocinonide cream. Fluocinonide is a synthetic corticosteroid for topical dermatologic use. The corticosteroids constitute a class of primarily synthetic steroids used topically as anti-inflammatory and antipruritic agents. Fluocinonide is practically insoluble in water and slightly soluble in ethanol. Fluocinonide cream may include fluocinonide with additional ingredients such as carbomer homopolymer type c (allyl pentaerythritol cross-linked), polyoxyl 20 cetostearyl ether, citric acid monohydrate, diethylene glycol monoethyl ether, polyethylene glycols, propylene glycol, sorbitan monostearate, trolamine. Various fluocinonide creams, such as 0.1% creams, are commercially available prescription corticosteroid medicine used on the skin (topical) to treat adults and children 12 years and older with certain skin conditions that cause red, flaky, and itchy skin. For psoriasis, for example, a thin layer of fluocinonide cream 0.1% may be applied once or twice daily to the affected skin areas as directed by a physician. For atopic dermatitis, a thin layer of fluocinonide cream 0.1% may be applied once daily to the affected skin areas as directed by a physician. A particular example of fluocinonide cream 0.1%, is Fluocinonide Cream 0.1%. Among other sources, Fluocinonide Cream 0.1% is manufactured by Taro Pharmaceuticals Inc. Brampton, Ontario, Canada L6T 1C1 and distributed by Taro Pharmaceuticals U.S.A., Inc., Hawthorne, NY 10532. Other manufactures or distributers may be used. Each gram of Fluocinonide Cream 0.1% contains 1 mg micronized fluocinonide in a topical base of carbomer 940 (carbopol 980), ceteareth-20, citric acid, diethylene glycol monoethyl ether (transcutol P), polyethylene glycol, propylene glycol, sorbitan monostearate, and trolamine. Other strengths of Fluocinonide cream may be used consistent with the compositions and methods described herein.

In one embodiment, the topical composition includes a fluocinonide cream 0.1% and one or more antifungals selected from those identified above or elsewhere herein and in an amount provided above or elsewhere herein. For example, the topical composition may include a fluocinonide cream 0.1% and an antifungal comprising an azole selected from itraconazole, clotrimazole, econazole, oxiconazole, ketoconazole, miconazole, voriconazole, sulconazole, fluconazole. In certain embodiments, the topical composition comprises Econazole Nitrate Cream 1% and a fluocinonide cream 0.1% in a ratio between approximately 5:1 to approximately 2:1, such as approximately 3:1. For example, the topical composition may comprise approximately 75% by weight Econazole Nitrate Cream 1% and approximately 25% by weight of a fluocinonide cream 0.1%, such as Fluocinonide Cream 0.1%. Other cream strengths may be used.

In various embodiments, the topical composition includes a commercially available clobetasol propionate cream. Clobetasol propionate is a synthetic corticosteroid for topical dermatologic use. Clobetasol propionate has anti-inflammatory, antipruritic, and vasoconstrictive properties. Clobetasol, an analog of prednisolone, has a high degree of glucocorticoid activity and a slight degree of mineralocorticoid activity. Clobetasol propionate creams are super-high potency corticosteroid formulations indicated for the relief of the inflammatory and pruritic manifestations of corticosteroid responsive dermatoses. Clobetasol propionate cream may be provided in various concentrations. Particular examples of such commercially available clobetasol propionate creams include Clobetasol Propionate Gel, Cream, or Ointments. Among other sources, Clobetasol Propionate Gel, Cream, and Ointment 0.05% are manufactured by Taro Pharmaceuticals Inc., Brampton, Ontario, Canada L6T 1C1 and distributed by Taro Pharmaceuticals U.S.A., Inc., Hawthorne, NY 10532. Other manufactures or distributers may be used. Clobetasol Propionate Gel 0.05% may be supplied in tubes (15 g, 30 g, 60 g). Each gram of the 0.05% Gel contains 0.5 mg clobetasol propionate in a base of carbomer 934P, propylene glycol, purified water, and sodium hydroxide. Clobetasol Propionate Cream 0.05% may also be supplied in tubes (15 g, 30 g, 45 g, 60 g). Each gram of the 0.05% Cream contains clobetasol propionate 0.5 mg in a cream topical base of cetyl alcohol, chlorocresol, citric acid, glyceryl monostearate, glyceryl stearate/polyethylene glycol 100 stearate, propylene glycol, purified water, sodium citrate, stearyl alcohol, and white wax. Clobetasol Propionate Ointment 0.05% may also be supplied in tubes (15 g). Each gram of the 0.05% Ointment contains clobetasol propionate 0.5 mg in a base of propylene glycol, sorbitan sesquioleate, and white petrolatum. Other strengths of clobetasol propionate cream may be used consistent with the compositions and methods described herein.

In one embodiment, the topical composition includes a clobetasol propionate cream, such as Clobetasol Propionate Gel, Cream, or Ointment 0.05%, and one or more antifungals selected from those identified above or elsewhere herein and in an amount provided above or elsewhere herein. For example, the topical composition may include a clobetasol propionate cream and an antifungal comprising an azole selected from itraconazole, clotrimazole, econazole, oxiconazole, ketoconazole, miconazole, voriconazole, sulconazole, fluconazole. In certain embodiments, the topical composition comprises Econazole Nitrate Cream 1% and a clobetasol propionate cream 0.05% in a ratio between approximately 5:1 to approximately 2:1, such as approximately 3:1. For example, the topical composition may comprise approximately 75% by weight Econazole Nitrate Cream 1% and approximately 25% by weight a clobetasol propionate cream 0.05%, such as Clobetasol Propionate Gel, Cream, or Ointment 0.05%.

In various embodiments, any of the above formulations of the topical composition may further include one or more additional actives. In one embodiment, the topical composition may include approximately 2% to approximately 5% antibiotic by weight. For example, the antibiotic may be selected from mupirocin, clindamycin, besifloxacin, cefazolin, ofloxacin, azithromycin, ceftazidime, natamycin, ciprofloxacin, gentamicin, vancomycin, tobramycin, clarithromycin, levofloxacin, moxifloxacin, Nystatin, or combinations thereof. In this or another embodiment, the topical composition may include approximately 0.5% and approximately 5% by weight local anesthetic. For example, the local anesthetic may be selected from lidocaine, amethocaine, benzocaine, prilocaine, or combinations thereof. In any of the above or another embodiment, the topical composition comprises approximately 0.5% to 5% non-steroidal anti-inflammatory (NSAID). For example, the NSAID may be selected from indomethacin, meloxicam, ibuprofen, dexibuprofen, diclofenac, ketoprofen, flurbiprofen, piroxicam, pranoprofen, or combinations thereof. In any of the above or another embodiment, the topical composition may comprise approximately 0.05% to approximately 1% by weight of one or more of amitriptyline, capsacin, diltiazem, clonidine, nefedipin, pentoxifylline, emedastine, gabapentin, ketamine, ketotifen, or rebamipide.

Also disclosed herein are methods of treating a patient for a fungal skin condition with associated inflammation. The method of treatment may include applying the topical composition to infected skin. In certain embodiments, 1 to 5 grams of the topical composition may be applied to affected skin areas. The amount and number of administrations per day may vary, but, generally, a three administration should not be exceeded per day.

In various embodiments, a method of treating a patient for a fungal skin condition with associated inflammation includes compounding a topical composition comprising any of the topical compositions described above or elsewhere herein.

In one example, the method of compounding the topical composition may include combining one or more of the corticosteroids described herein to a topical base cream as also described herein. The method may further include combining one or more antifungals, such as any of the antifungals described herein, to the topical base. In one embodiment, the method includes crushing one or more commercial tablets of a corticosteroid and adding the powder obtained from the crushed tablets of corticosteroid to the topical base. In this or another embodiment, the method includes crushing one or more commercial tablets of an antifungal and adding the powder obtained from the crushed tablets of antifungal to the topical base. In some embodiments, compounding the corticosteroid, antifungal, and topical base cream includes adding bulk powders of one or more corticosteroids, antifungals, or both to the topical base and mixing. In embodiments that include additional actives, such actives may be obtained from bulk sources or crushed tablets and also combined with the topical base. Powders may be wetted prior to addition to the topical base, e.g., with dimethyl sulfoxide (DMSO), an alcohol, water, e.g., purified water, water for irrigation, water for injection, or a sterile water, to form a paste. In some embodiments, powders are not wetted prior to addition to the topical base.

According to one embodiment, a method of compounding the topical composition for treating a fungal skin condition and associated inflammation includes combining fluticasone, or pharmaceutically acceptable salt, ester, or derivative thereof, itraconazole, or pharmaceutically acceptable salt, ester, or derivative thereof, and a topical base. Combining may include adding and mixing the components together. The components may be combined all at once or portions of one or more of the components may be added to other components or portions thereof in increments until combining of the components is achieved. The itraconazole may be combined in an amount between approximately 3% and approximately 8% by weight of the compounded topical composition. The fluticasone may be combined as fluticasone propionate in an amount between approximately 0.5% and 2.5% by weight of the compounded topical composition. The topical base may include Base C and a water miscible base, e.g., Spira-Wash™ Gel. The water miscible base and Base C may be present in a ratio of water miscible base to Base C between approximately 8:1 and approximately 9:1. In one example, the topical base may be combined with the fluticasone propionate and itraconazole in an amount between approximately 5% and approximately 15% Base C by weight of the compounded topical composition and between approximately 90% and approximately 75% Spira-Wash™ Gel by weight of the compounded topical composition. The Base C and Spira-Wash™ Gel may be added together or separate. In one particular example, itraconazole may be combined in an amount approximately 5% by weight of the compounded topical composition, fluticasone propionate may be combined in an amount approximately 1% by weight of the compounded topical composition, Base C may be combined in an amount approximately 10% by weight of the compounded topical composition, and Spira-Wash™ Gel may be combined in an amount approximately 84% by weight of the compounded topical composition. In one formulation, the itraconazole and fluticasone are combined with the topical base or components thereof in the form of bulk powders.

In one embodiment, the method of compounding the topical composition comprises combining itraconazole, fluticasone, and a water miscible topical base, such as Spira-Wash™ Gel. In one example, compounding a topical composition comprising 5% itraconazole by weight and 1% fluticasone by weight, the method includes, for each 100 gm of composition, combining 5 gm itraconazole EP micronized and 1 gm fluticasone propionate micronized with a topical base cream comprising 10 gm Base C (Polyethylene Glycol 300 MW, NF Liquid), and 84 gm water miscible base (Spira-Wash™ Gel in this example). Combining may include mixing the ingredients. Mixing may be performed in an appropriate size Electronic Mortar and Pestle (EMP) Jar. The ingredients may be mixed in the EMP for three minutes on a medium setting. The mixture may then be processed through an ointment mill (setting of two) two times to reduce the particle size of the active ingredients and to eliminate grittiness of the final preparation. The preparation may be packaged in appropriate containers, preferably protected from light and in an air-tight container. A method of treating a patient for a fungal skin condition with associated inflammation with the above topical composition may include applying up to 4 gm per day of the topical composition to the affected skin area. For example, approximately 2 gm of the topical composition may be applied to affected skin area two times daily (up to 4 gm per day).

In one embodiment, the method of compounding the topical composition comprises combining the antifungal and a commercially available fluocinonide cream, such as fluocinonide cream 0.1% (e.g., Fluocinonide Cream 0.1%). A suitable amount of the antifungal may be added to the fluocinonide cream in powder form obtained from bulk antifungal powder or crushed tablets of antifungal. In embodiments that include additional actives, such actives may also be obtained in powder form from bulk sources or crushed tablets and added to the fluocinonide cream. Powders may be wetted prior to addition to the cream, e.g., with dimethyl sulfoxide (DMSO), an alcohol, water, e.g., purified water, water for irrigation, water for injection, or a sterile water, to form a paste. In some embodiments, powders are not wetted.

A method of treating a patient for a fungal skin condition with associated inflammation with the above topical composition may include applying up to 4 gm per day of the topical composition to the affected skin area. For example, approximately 2 gm of the topical composition may be applied to affected skin area two times daily (up to 4 gm per day).

In one embodiment, the method of compounding the topical composition comprises addition of the antifungal to a commercially available clobetasol propionate cream 0.05%, such as Clobetasol Propionate Gel, Cream, or Ointment 0.05%. A suitable amount of the antifungal may be added to the clobetasol propionate cream in powder form obtained from bulk antifungal powder or crushed tablets of antifungal. In embodiments that include additional actives, such actives may also be obtained in powder form from bulk sources or crushed tablets and added to the clobetasol propionate cream. Powders may be wetted prior to addition to the cream, e.g., with dimethyl sulfoxide (DMSO), an alcohol, water, e.g., purified water, water for irrigation, water for injection, or a sterile water, to form a paste. In some embodiments, powders are not wetted.

In one embodiment, the method of compounding the topical composition comprises addition of the corticosteroid to a commercially available econazole nitrate cream, such as Econazole Nitrate Cream 1%. A suitable amount of corticosteroid may be added to econazole nitrate cream in powder form obtained from bulk antifungal powder or crushed tablets of antifungal. In embodiments that include additional actives, such actives may also be obtained in powder form from bulk sources or crushed tablets and combined with the fluocinonide cream. Powders may be wetted prior to addition to the cream, e.g., with dimethyl sulfoxide (DMSO), an alcohol, water, e.g., purified water, water for irrigation, water for injection, or a sterile water, to form a paste. In some embodiments, powders are not wetted before addition to the cream.

In one embodiment, the method of compounding the topical composition comprises mixing a commercially available econazole nitrate cream, such as Econazole Nitrate Cream 1%, with a commercially available fluocinonide cream, such as fluocinonide cream 0.1% (e.g., Fluocinonide Cream 0.1%), a commercially available clobetasol propionate cream 0.05%, such as Clobetasol Propionate Gel, Cream, or Ointment 0.05%, or both. For example, a method of compounding the topical composition described above having a 3:1 ratio of Econazole Nitrate Cream 1% to Fluocinonide Cream 0.1% may include mixing three parts Econazole Nitrate Cream 1% for every one part Fluocinonide Cream 0.1% to provide a final topical composition having 0.75% Econazole Nitrate Cream 1% by weight and 0.025% Fluocinonide Cream 0.1% by weight. A method of treating a patient for a fungal skin condition with associated inflammation with the above topical composition may include applying up to 8 gm per day of the topical composition to the affected skin area. For example, approximately 4 gm of the topical composition may be applied to affected skin area two times daily (up to 8 gm per day).

As a further example, a method of compounding the topical composition described above having a 3:1 ratio of Econazole Nitrate Cream 1% to Clobetasol Propionate Ointment 0.05% may include mixing three parts Econazole Nitrate Cream 1% for every one part Clobetasol Propionate Ointment 0.05% to provide a final topical composition of 0.75% Econazole Nitrate Cream 1% by weight and 0.00125% Clobetasol Propionate Ointment 0.05% by weight. A method of treating a patient for a fungal skin condition with associated inflammation with the above topical composition may include applying up to 8 gm per day of the topical composition to the affected skin area. For example, approximately 4 gm of the topical composition may be applied to affected skin area two times daily (up to 8 gm per day).

In one embodiment, a method of treating a patient for a fungal skin condition with associated inflammation includes administering a commercially available econazole nitrate cream to an affected skin area. For example, the method may include administering up to 6 gm Econazole Nitrate Cream 1% per day, such as 3 gm two times per day, to the affected skin area. The method may further include administering a commercially available fluocinonide cream to the affected skin area. For example, the method may include administering up to 2 gm of Fluocinonide Cream 0.1% per day, such as 1 gm two times per day, to the affected skin area. The method may include applying the econazole nitrate cream and fluocinonide cream to the affected skin area substantially at the same time, sequentially, or at a timed interval, e.g., after an hour, two hours, three hours, four hours, five hours, or six hours after application of the other cream.

In one embodiment, a method of treating a patient for a fungal skin condition with associated inflammation includes administering a commercially available econazole nitrate cream to an affected skin area. For example, the method may include administering up to 6 gm Econazole Nitrate Cream 1% per day, such as 3 gm two times per day, to the affected skin area. The method may further include administering a commercially available clobetasol propionate cream to the affected skin area. For example, the method may include administering up to 2 gm of Clobetasol Propionate Gel, Cream, or Ointment 0.05% per day, such as 1 gm two times per day, to the affected skin area. The method may include applying the econazole nitrate cream and clobetasol propionate cream to the affected skin area substantially at the same time, sequentially, or at a timed interval, e.g., after an hour, two hours, three hours, four hours, five hours, or six hours after application of the other cream.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. Further, active agents identified herein may include pharmaceutically acceptable salts, esters, or derivative thereof, which may further include prodrugs thereof. In this manner, Applicant reserves the right to amend the claims during prosecution to add features as variously described in this specification, and such amendments comply with the requirements of 35 U.S.C. §§ 112(a) and 132(a).

Numerical limitations modified by approximately include the number +/−10% of the number. The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of treating a patient for a fungal skin condition and associated inflammation, the method comprising:
    applying Econazole Nitrate Cream 1% w/w to affected skin area;
    applying at least one of a Fluocinonide Cream 0.1% w/w or Clobetasol Propionate Cream, Gel, or Ointment 0.05% w/w to the affected skin area.

2. The method of claim 1, wherein applying the Econazole Nitrate Cream 1% w/w comprises applying up to 3 gm of the cream to the affected skin area two times daily.

3. The method of claim 2, comprising applying the Fluocinonide Cream 0.1% w/w, wherein applying the Fluocinonide Cream 0.1% w/w comprises applying up to 1 gm of the cream to the affected skin area two times daily.

4. The method of claim 3, comprising applying the Clobetasol Propionate Cream, Gel, or Ointment 0.05% w/w, wherein applying the Clobetasol Propionate Cream, Gel, or Ointment 0.05% w/w comprises applying up to 1 gm of the cream, gel, or ointment to the affected skin area two times daily.

5. The method of claim 4, wherein the Clobetasol Propionate Cream, Gel, or Ointment 0.05% w/w is Clobetasol Propionate Ointment 0.05% w/w.

6. The method of claim 1, wherein applying the Econazole Nitrate Cream 1% w/w comprises applying up to 3 gm of the cream to the affected skin area two times daily, wherein applying the at least one of Fluocinonide Cream 0.1% w/w or Clobetasol Propionate Cream, Gel, or Ointment 0.05% w/w comprises applying up to 1 gm of Fluocinonide Cream 0.1% w/w or 1 gm of Clobetasol Propionate Ointment 0.05% w/w to the affected skin area two times daily.

7. The method of claim 6, wherein applying Econazole Nitrate Cream 1% w/w and the at least one of the Fluocinonide Cream 0.1% w/w or Clobetasol Propionate Ointment 0.05% w/w comprising applying the Econazole Nitrate Cream 1% w/w and the at least one of the Fluocinonide Cream 0.1% w/w or Clobetasol Propionate Ointment 0.05% w/w at substantially the same time to the affected skin area.

* * * * *